United States Patent [19]

Whiteside et al.

[11] Patent Number: 5,342,366
[45] Date of Patent: Aug. 30, 1994

[54] SURGICAL INSTRUMENTS FOR HIP REVISION

[75] Inventors: Leo A. Whiteside, Chesterfield, Mo.; Roy C. Wiley, Warsaw, Ind.

[73] Assignee: Biomet, Inc., Warsaw, Ind.

[21] Appl. No.: 838,528

[22] Filed: Feb. 19, 1992

[51] Int. Cl.⁵ .................. A61F 5/04; A61B 17/56
[52] U.S. Cl. ................................ 606/86; 606/102
[58] Field of Search .................. 623/16, 18, 20, 22, 623/23; 606/102, 86, 87, 96

[56] References Cited

U.S. PATENT DOCUMENTS

| | | |
|---|---|---|
| 2,682,265 | 6/1954 | Collison . |
| 2,719,522 | 10/1955 | Hudack . |
| 2,765,787 | 10/1956 | Pellet . |
| 2,781,758 | 2/1957 | Chevalier . |
| 2,785,673 | 3/1957 | Anderson . |
| 3,064,645 | 11/1962 | Ficat . |
| 3,067,740 | 12/1962 | Haboush . |
| 3,102,536 | 9/1963 | Rose et al. . |
| 3,683,421 | 8/1972 | Martinie . |
| 3,806,957 | 4/1974 | Shersher . |
| 3,815,590 | 6/1974 | Deyerle ............................ 606/102 |
| 3,818,512 | 6/1974 | Shersher . |
| 3,820,167 | 6/1974 | Sivash . |
| 3,863,273 | 2/1975 | Averill . |
| 3,906,550 | 9/1975 | Rostoker et al. . |
| 3,918,441 | 11/1975 | Getscher . |
| 3,987,499 | 10/1976 | Scharbach et al. . |
| 3,996,625 | 12/1976 | Noiles . |
| 4,051,559 | 10/1977 | Pifferi . |
| 4,115,875 | 9/1978 | Rambert et al. . |
| 4,404,691 | 9/1983 | Buning et al. . |
| 4,459,708 | 7/1984 | Buttazzoni . |
| 4,488,319 | 12/1984 | von Recum . |
| 4,520,511 | 6/1985 | Gianezio et al. . |
| 4,532,660 | 8/1985 | Field . |
| 4,578,081 | 3/1986 | Harder et al. . |
| 4,608,055 | 8/1986 | Morrey et al. . |
| 4,658,808 | 4/1987 | Link . |
| 4,662,891 | 5/1987 | Noiles .................. 623/23 |
| 4,676,797 | 6/1987 | Anapliotis et al. . |
| 4,676,798 | 6/1987 | Noiles .................. 623/23 |
| 4,678,472 | 7/1987 | Noiles .................. 623/23 |
| 4,693,724 | 9/1987 | Rhenter et al. .......... 623/23 |
| 4,718,916 | 1/1988 | Morscher .............. 623/23 |

(List continued on next page.)

FOREIGN PATENT DOCUMENTS

| | | |
|---|---|---|
| 0163121A1 | of 1985 | European Pat. Off. . |
| 0190981A1 | of 1986 | European Pat. Off. . |
| 0198163A2 | of 1986 | European Pat. Off. . |
| 2318396 | of 1974 | Fed. Rep. of Germany . |
| 3538654A1 | of 1987 | Fed. Rep. of Germany . |

(List continued on next page.)

OTHER PUBLICATIONS

Article, Joint Medical Products Corporation, 1990, "Should Your Intraoperative Solutions Be Limited to One Design?".

(List continued on next page.)

*Primary Examiner*—David Isabella
*Attorney, Agent, or Firm*—Harness, Dickey & Pierce

[57] ABSTRACT

A modular hip prosthesis operable to engage the cortical material in a host femur having a metaphysis and an intramedullary canal. The modular hip prosthesis includes a modular metaphyseal segment which is able to be inserted into the metaphysis of the host femur. The modular metaphyseal segment includes an axial cone portion and a cervical cone portion. The modular hip prosthesis further includes a modular diaphyseal segment which is able to be inserted into the intramedullary canal and being removably secured to the modular metaphyseal segment. Finally, the modular hip prosthesis includes a modular head which is able to engage the modular metaphyseal segment and is detached from the modular diaphyseal segment.

Also disclosed is surgical instrumentation for use in implanting a medical device. The surgical instrumentation includes a template having a plurality of scaled markings disposed thereon. The surgical instrumentation also includes a plurality of surgical instruments also having scaled markings disposed thereon. The positions of the scaled markings on the surgical instruments have a correspondence with the position of the scaled markings on the template.

5 Claims, 6 Drawing Sheets

U.S. PATENT DOCUMENTS

| | | | |
|---|---|---|---|
| 4,728,335 | 3/1988 | Jurgutis | 623/18 |
| 4,777,942 | 10/1988 | Frey et al. | 623/23 |
| 4,790,852 | 12/1988 | Noiles | 623/23 |
| 4,822,370 | 4/1989 | Schelhas | 623/23 |
| 4,840,632 | 6/1989 | Kampner | 623/23 |
| 4,851,007 | 7/1989 | Gray | 623/23 |
| 4,865,608 | 9/1989 | Brooker, Jr. | 623/23 |
| 4,936,863 | 6/1990 | Hofmann | 623/18 |
| 4,995,883 | 2/1991 | Demane et al. | 623/18 |
| 5,002,581 | 3/1991 | Paxson et al. | 623/18 |
| 5,013,318 | 5/1991 | Spranza, III | 606/102 |
| 5,047,033 | 9/1991 | Fallin | 623/18 |
| 5,080,685 | 1/1992 | Bolesky et al. | |
| 5,122,146 | 6/1992 | Chapman et al. | 606/102 |
| 5,181,928 | 1/1993 | Bolesky et al. | 623/23 |

FOREIGN PATENT DOCUMENTS

| | | | |
|---|---|---|---|
| 3538654A | 1/1987 | Fed. Rep. of Germany . | |
| 2378505 | of 1978 | France . | |
| 2576793 | of 1986 | France . | |
| 0063034 | 12/1940 | Norway | 606/102 |
| 8502555 | 8/1983 | PCT Int'l Appl. . | |
| 8503426 | 8/1985 | PCT Int'l Appl. . | |
| 1026790 | 7/1983 | U.S.S.R. | 606/102 |

OTHER PUBLICATIONS

Brochure, Joint Medical Products Corporation, "The S-ROM ™ Total Hip System: Select to Fit & Fill".

Brochure, Joint Medical Products Corporation, 1990, "The S-ROM ™ TRI-VERSION ™ Femoral Stem System Using ZT ™ Graduated Proximal Sleeves Surgical Technique".

Article, *Orthopedics Today*, Nov. 1989, "S-ROM Stem and Sleeve Combination Uses Standard Parts for Custom Fits".

Article, Hugh U. Cameron, et al., 1990, "An International Multi-Center Study on Thigh Pain in Total Hip Replacements".

Article, David A. Fisher, et al., *SEMINARS IN ARTHROPLASTY*, vol. 1, No. 1, Jul. 1990, "Evaluation of the Design and Clinical Performance of Cementless Acetabular Components".

Article, Hugh U. Cameron, et al., "S-ROM ™ Modular Stem System: Design Features and Early Clinical Results With a Modular Proximally Fixed Low Bending Stiffness Uncemented Total Hip Replacements".

Article, Hugh U. Cameron, M. D., *Sports Medicine News*, Apr. 1990, "Arthroplasty: Factors Inducing Thigh Pain After Uncemented THR Identified".

Article, Paul D. Postak, B. S., et al., "A New Method of Fatigue Testing for Proximally Supported Femoral Stems".

Article, Hugh U. Cameron, *Orthopedics Today*, Nov. 1989 "S-ROM Stem and Sleeve Combination Uses Standard Parts for Custom Fits".

DePoy Manufacturing "Aids for the Fracture Surgeon", Journel of Bone & Joint Surgery Oct. 1953, vol. 35B, p. 14.

Dow-Corning-Wright, "Whiteside total Hip System", 1985.

SURGICAL INSTRUMENTS FOR HIP REVISION

BACKGROUND OF THE INVENTION

This invention relates generally to a prosthetic total hip joint replacement system, and more specifically, to a modular hip prosthesis having modular components.

A natural hip joint may undergo degenerative changes due to a variety of etiologies. When these degenerative changes become so far advanced and irreversible, it may ultimately become necessary to replace the natural hip joint with a prosthetic hip. When implantation of such a hip joint prosthesis becomes necessary, the head of the natural femur is first resected and then a cavity is created within the intramedullary canal of the host femur for accepting and supporting the prosthetic hip.

Because different patients have femurs of various shapes, it is necessary to have available different appropriately structured prosthetic hip joint assemblies to accommodate these different shapes. Moreover, different patients having host femurs with substantially the same sized intramedullary canals may have femoral necks of different shapes and lengths and vice versa. Consequently, a prosthetic hip joint assembly that has a distal portion that is appropriate for one host femur may not have a metaphyseal portion which would provide the best fit for the femoral neck of that host femur. Accordingly, the most desirable fit may not always be possible, resulting in adverse affects on hip motion and patient comfort.

Different prosthetic hip joint assemblies have addressed this problem in the prior art. Of those, one includes a prosthetic hip joint assembly including a prosthesis body having a midsection portion and an upper neck portion adapted to carry an artificial femoral head. A plurality of tubular extension sleeves are adaptable to engage a stem portion of the midsection portion. The extension sleeves can be of varying lengths and curvatures such that an extension sleeve can be selected that will more aptly engage the intramedullary canal of a host femur. Additionally, specially configured pads can be attached to the midsection portion for increasing the cross-sectional shape of the body of the prosthesis to effectively engage the walls of the reamed cavity within the host femur.

SUMMARY OF THE INVENTION

The present invention provides a modular hip prosthesis assembly which includes separate, universally engageable components including a diaphyseal segment, a metaphyseal segment, and an artificial femoral head, such that the different components can be interchangeably engageable with each other to provide the most acceptable fit within a host femur. The invention also includes a surgical procedure operable to surgically prepare the host femur for acceptance of the modular hip prosthesis assembly.

An advantage of the present invention is that a modular hip prosthesis as described herein results in a more adaptable artificial hip joint prosthesis to the different structural configurations of a particular patient.

Another advantage of the present invention is a surgical procedure for accurately and easily determining the size of the different modular components of the modular hip prosthesis so as to provide the most desirable fit for a particular patient.

Yet another advantage of the present invention is a set of surgical instruments adaptable to implant the modular hip joint prosthesis assembly into a host femur in an efficient manner. In this regard, a related object of the present invention is to avoid the use of rasps which are difficult to use.

A further advantage of the present invention is a modular hip prosthesis that is more securely engageable with the intramedullary canal of a host femur. In this regard, a related advantage is to provide a modular hip prosthesis that optimizes physiological transfer of load.

The invention, in one form thereof, provides a modular hip prosthesis which includes a diaphyseal segment having an elongated stem portion, and a metaphyseal segment having an axial cone portion and a cervical cone portion. The diaphyseal segment further includes a tapered neck portion at its proximal end engageable in a tapered bore within the metaphyseal segment such that the metaphyseal segment and the diaphyseal segment are attachable in a friction fit. Additionally, the metaphyseal segment includes a tapered neck portion operable to extend within a femoral neck which is engageable within a tapered bore in a modular femoral head. Desirably, each of the diaphyseal segment, the metaphyseal segment, and the modular head are interchangeable with other diaphyseal segments, metaphyseal segments and modular heads to enable a wide flexibility in selecting an appropriately configured hip prosthesis assembly.

The invention, in another form thereof, provides surgical instrumentation that is used for implanting medical devices. The surgical instrumentation includes a template having plurality of scaled markings disposed thereon. The surgical instrumentation further includes plurality of surgical instruments also having scaled markings disposed thereon. The position of the scaled markings disposed on the plurality of surgical instruments correspond with the position of the scaled markings on the template.

The invention, in a further form thereof, includes a set of surgical instruments for use in implanting a hip prosthesis. The surgical instruments include a distal canal reamer operable to ream a cavity in the host femur for receiving the diaphyseal segment. The surgical instruments further include a metaphyseal reamer that is operable to ream a cavity in the host femur for receiving the metaphyseal segment. A femoral neck reamer is also provided that is able to ream the neck portion of the femur as well as a femoral cutting guide that is used in conjunction with the femoral neck reamer.

Additional objects, advantages, and features of the present invention will become apparent from the following description and appended claims, taken in conjunction with the accompanying drawings.

DETAILED DESCRIPTION OF THE PREFERRED EMBODIMENT

The following discussion of the preferred embodiment of the present invention is merely exemplary in nature and is in no way intended to limit the invention or its application or uses.

Figures 1, 2:
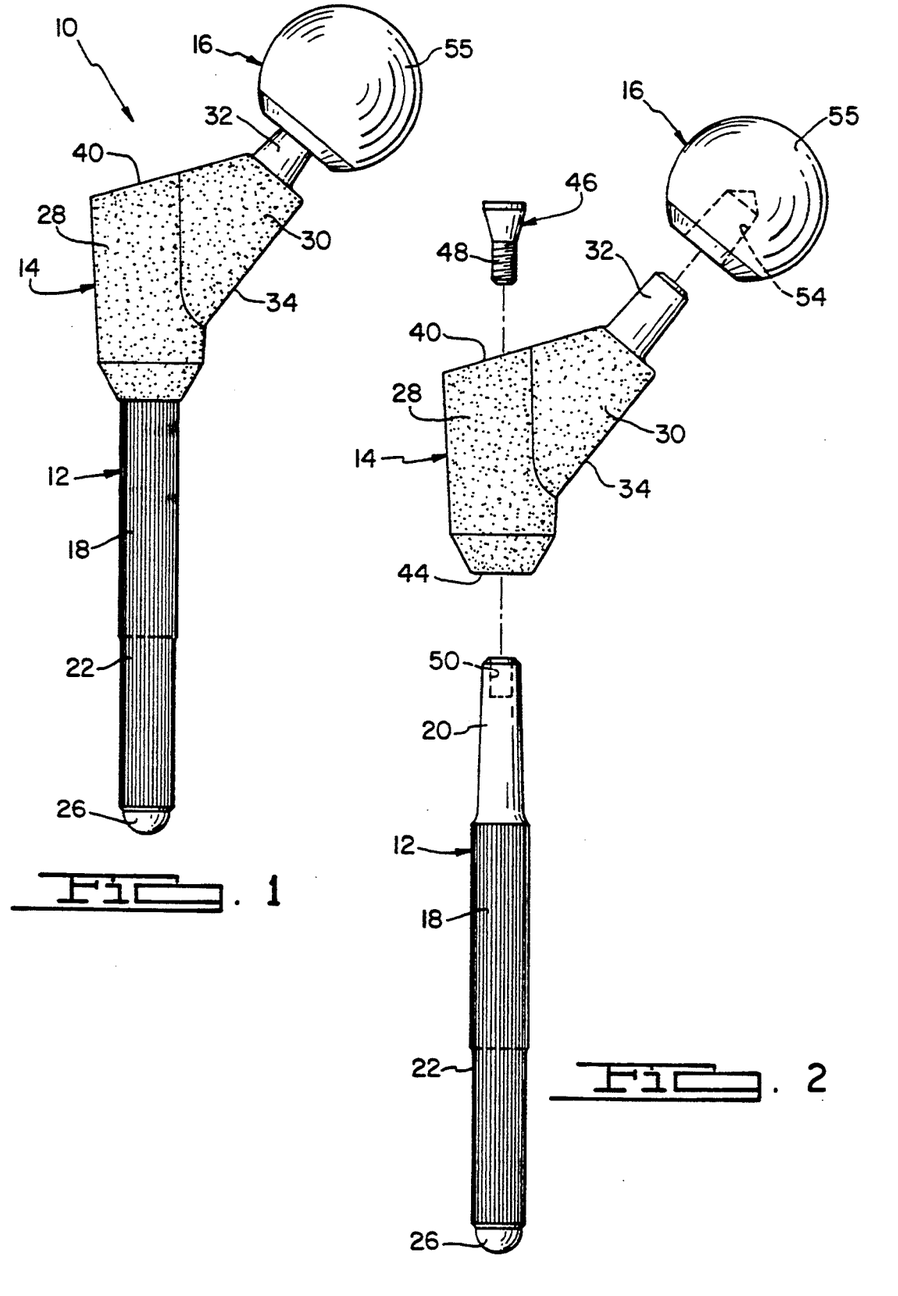
FIG. 1 is an anterior view of a modular hip prosthesis according to the teachings of the preferred embodiment of the present invention.
FIG. 2 is an exploded anterior view of the modular hip prothesis shown in FIG. 1 illustrating the relationship between the various modular components of the preferred embodiment of the presented invention.

Referring now to FIG. 1, a modular hip prosthesis 10 according to the preferred embodiment of the present invention is shown. The modular hip prosthesis 10 is used to replace a natural hip after the natural hip has degenerated. The modular hip prosthesis 10 includes a diaphyseal segment 12, a metaphyseal segment 14 and a modular head 16. As used herein, the diaphyseal segment 12 will be used to represent one of a plurality of diaphyseal segments which are similar to that which is shown in FIG. 1 but which are of different sizes. Similarly, the metaphyseal segment 14 and the modular head 16 will also be used to represent one of a plurality of similar components which are of different sizes. The metaphyseal segment 14 is able to engage the diaphyseal segment 12 as well as the modular head 16 independent of the relative sizes of these components. As more fully discussed below, this modularity between the diaphyseal segment 12, the metaphyseal segment 14, and the modular head 16 permits the modular hip prosthesis 10 to provide a wider degree of flexibility in achieving the most desirable shape for different patients.

Turning to FIG. 2, an exploded view of the modular hip prosthesis 10 according to the preferred embodiment of the present invention is shown. The diaphyseal segment 12 is an elongated cylindrical member that is able to engage a specially reamed diaphyseal cavity in a host femur and is used to provide stability for the modular hip prosthesis 10. The diameter of the diaphyseal segment 12 is selected such that the lower portion of the diaphyseal segment 12 (e.g., approximately the lowermost 4 centimeters) is able to be located within the intramedullary canal of the host femur adjacent to cortical bone. The diaphyseal segment 12 comprises an elongated stem portion 18 as well as a tapered portion 20. The tapered portion 20 of the diaphyseal segment 12 has substantially the same diameter for each size so that each size of the diaphyseal segment 12 can engage any size of metaphyseal segment 14. The elongated stem portion 18 has a plurality of anti-rotation flutes 22 circumferentially located which extend axially on the exterior surface of the elongated stem portion 18. The anti-rotation flutes 22 extend approximately 0.5 mm above the surface of the elongated stem portion 18 and are used to engage the walls of the diaphyseal cavity of the host femur so as to limit rotational movement of the diaphyseal segment 12 with respect to the host femur.

The diaphyseal segment 12 further includes a slotted section 24 that is located at the distal end of the elongated stem portion 18. The slotted section 24 extends superiorly approximately 1½" from the rounded end portion 26 of the elongated stem portion 18. The rounded end portion 26 reduces the possibility of distal impingement of the elongated stem portion 18 against the diaphyseal cavity. The slotted section 24 permits the diaphyseal segment 12 to flex in conjunction with specific movements of patients during ordinary or routine movements such as when rising from a chair so as also to reduce the possibility of distal impingement of the diaphyseal cavity with the elongated stem portion 18. While the diaphyseal segment 12 may be made from extra low interstitial Ti-6A1-4V, other suitable materials may be used.

Figure 3:
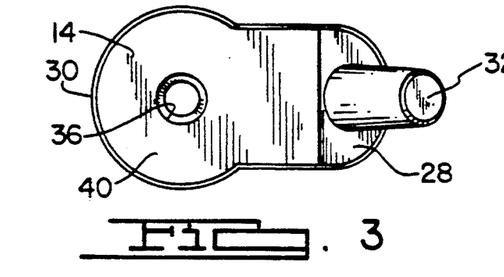
FIG. 3 is a top view of metaphyseal segment of the modular hip prosthesis shown in FIG. 1.
Figure 4:
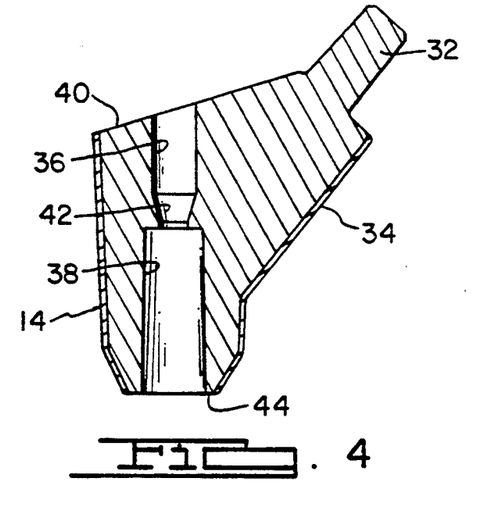
FIG. 4 is a cross-sectional view of the metaphyseal segment of the modular hip prosthesis shown in FIG. 1.

The metaphyseal segment 14 will now be described in greater detail. The metaphyseal segment 14 includes an axial cone portion 28 and a cervical cone portion 30. The axial cone portion 28 is operable to be located within the superior axial portion of the metaphyseal cavity formed in the host femur, while the cervical cone portion 30 is operable to be located within the neck portion of the host femur. The cervical cone portion 30 of the metaphyseal segment 14 includes a neck portion 32 as well as a specially shaped surface 34. The neck portion 32 of the metaphysical segment 14 is able to engage an orifice in the modular head 16 so as to secure the modular head 16 to the metaphyseal segment 14 as will be more fully described below. The specially shaped surface 34 extends substantially the entire length of the neck portion of the host femur and is operable to support the metaphyseal segment 14 on the hard cortical material of the neck portion. By locating the cervical cone portion 30 in this manner, much of the force transferred by the modular hip prosthesis 10 to the host femur is absorbed by the cortical bone in the femoral neck. Because the metaphyseal segment 14 transfers load to the host femur in this manner, torsional loading of the modular hip prosthesis 10 is absorbed by the relatively long moment arm associated with the neck portion of the host femur. This increases the rotational stability of the modular hip prosthesis 10 as well as provides for physiological transfer of load along the trabecular path.

To permit the metaphyseal segment 14 to be secured to the diaphyseal segment 12, the metaphyseal segment 14 further comprises a first bore 36 and a second bore 38. The first bore 36 extends from the superior surface 40 of the metaphyseal segment 14 distally toward a tapered portion 42 located within the metaphyseal segment 14, while the second bore 38 extends from the inferior surface 44 of the metaphyseal segment 14 superiorly to the tapered portion 42. The second bore 38 of the metaphyseal segment 14 is of sufficient diameter so as to be able to frictionally engage the tapered portion 20 of the diaphyseal segment 12, while the first bore 36 is of a sufficient diameter so as to be able to receive a segmental locking screw 46. The segmental locking screw 46 has a threaded portion 48 that is able to engage an internally threaded bore 50 located at the superior portion of the diaphyseal segment 12. Accordingly, when the tapered portion 20 of the diaphyseal segment 12 is inserted into the second bore 38 of the metaphyseal segment 14, the segmental locking screw 46 is able to engage the internally threaded bore 50 of the diaphyseal segment 12 thereby securing the metaphyseal segment 14 to the diaphyseal segment 12. While the metaphyseal segment 14 may be made from extra low interstitial Ti-6A1-4V, other suitable materials may be used.

The modular head 16 will now be described in greater detail. The modular head 16 includes an orifice 54 that is able to receive the neck portion 32 of metaphyseal segment 14. In this regard, the orifice 54 is such that the modular head 16 is engageable in a friction fit with respect to the neck portion 32 of the metaphyseal segment 14 regardless of the size of the metaphyseal segment 14. In a preferred embodiment, the neck portion 32 and the orifice 54 are tapered in order to provide a locking frictional engagement when the modular head 16 engages the metaphyseal segment 14. The modular head 16 further includes an articulating surface 55 that is able to articulate with an acetabular component (not shown). While the modular head 16 may be made from zirconia ceramic or cobalt chromium alloy, other suitable materials may be used.

Figure 5:
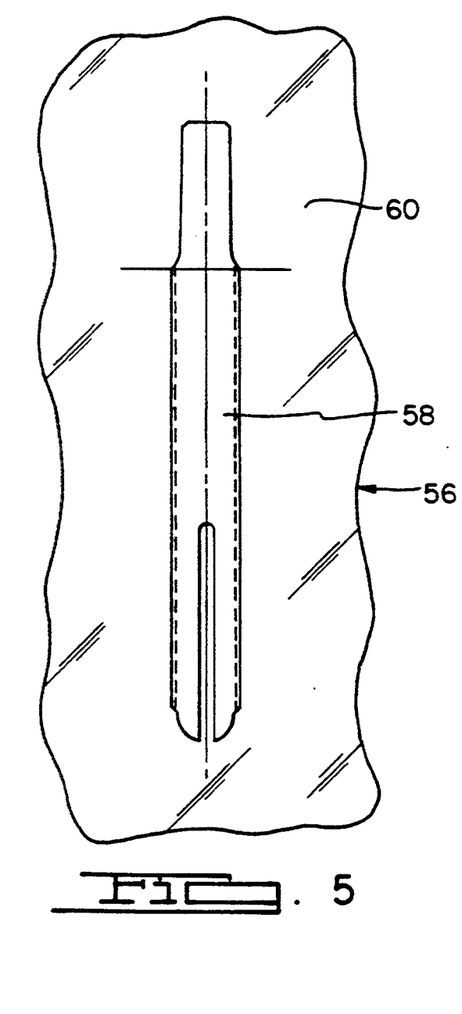
FIG. 5 is an elevational view of a template used during the implantation of the modular hip prosthesis shown in FIG. 1 according to the preferred method of the present invention.

To provide means for selecting the size of the diaphyseal segment 12, a first template 56 is provided. The first template 56 contains an image 58 of the diaphyseal segment 12 which is located on a transparent substrate 60. The first template 56 is used for selecting the appropriate size for the diaphyseal segment 12 for a particular implantation. As more fully described below, the surgeon uses the first template 56 to select the particular width of the diaphyseal segment 12 so that the lower portion of the diaphyseal segment 12 will engage cortical bone in the intramedullary canal once implanted.

Figure 6:
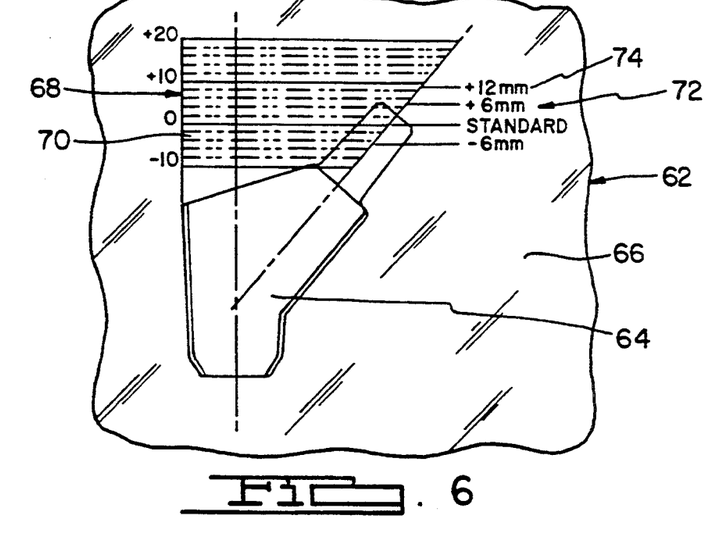
FIG. 6 is an elevational view of another template used during the implantation of the modular hip prosthesis shown in FIG. 1 according to the preferred method of the present invention.

To provide means for selecting the size of the metaphyseal segment 14, a second template 62 is provided. The second template 62 includes an image 64 of the metaphyseal segment 16 that is disposed on a transparent substrate 66. In addition, the second template 62 includes a longitudinal scale 68 having scaled markings 70 that are used to measure the relative height of the greater trochanter. The position of the scale markings 70 on the longitudinal scale 68 correspond to the position of similar scaled markings on the surgical instruments used to implant the modular hip prosthesis 10 which are described below. Finally, the second template 62 further includes a diagonal scale 72 which is used to select the size of the modular head 16 that is to be used with the modular hip prosthesis 10 for a particular patient. The manner in which the second template 62 is used will be more fully described below with respect to the implantation procedure of the present invention.

The method of implanting the modular hip prosthesis 10 will now be described with reference to FIGS. 7(A-)-(K). Once a radiograph 76 has been taken of the hip that is to be replaced a suitable acetabular component (not shown) is selected which may involve the use of a suitably sized template as is known in the art. If such a template is used, the surface of the acetabular component is placed concentrically with the subchondral bone.

Figure 7A:
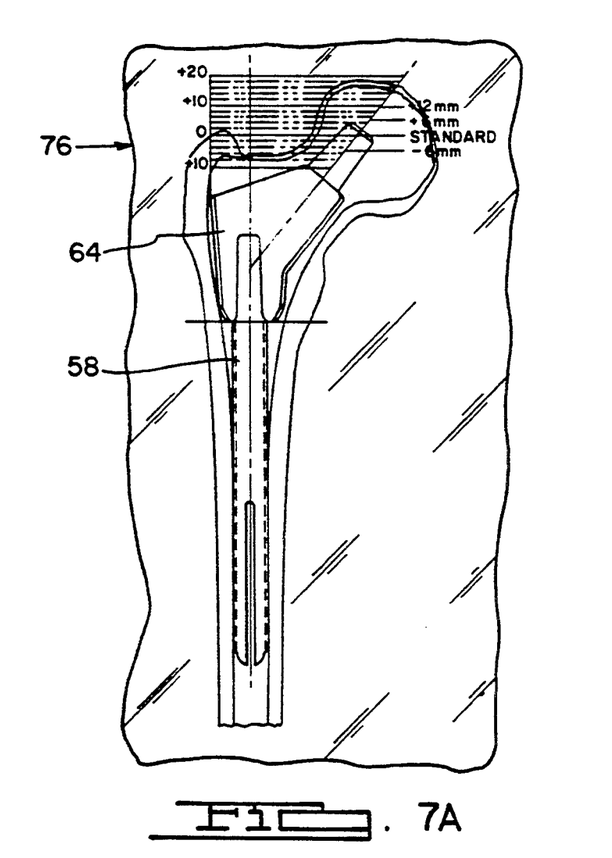
FIGS. 7(A)–(K) illustrate the method for implementing the modular hip prosthesis shown in FIG. 1 according to the teachings of the preferred embodiment of the present invention.

Once the acetabular component is chosen, the first template 56 and the second template 62 are then aligned on the radiograph 76 such that they are located in the position that corresponds to the positions where the diaphyseal segment 12 and the metaphyseal segment 14 will ultimately be located within the host femur 78. In this regard, the first template 56 is disposed on the radiograph 76 such that the centerline of the diaphyseal segment 12 is placed collinear with the central axis of the host femur. A proximal-to-distal positioning of the first template 56 can be estimated by orienting the bottom of the tapered portion 20 of the diaphyseal segment 12 with the center of the lesser trochanter. The surgeon can then determine the proximity of the cortical bone in the intramedullary canal to the image 58 of the elongated stem portion 18 of the diaphyseal segment 12 and therefore select which size of diaphyseal segment 12 should be used. In the preferred embodiment, there are several templates resembling the first template 56, each having an image of a different size of diaphyseal segment 12 disposed thereon so as to assist the surgeon in selecting which size of diaphyseal segment 12 will most closely mate with the host femur 78.

The second template 62 is then disposed on the radiograph 76 such that the centerline of the image 64 of the metaphyseal segment 14 is aligned with the centerline of the diaphyseal segment 12 of the first template 56. In addition, the portion of the image 64 of the metaphyseal segment 14 corresponding to the specially shaped surface 34 is located adjacent to the inner surface of the cortex of the neck portion 86 as indicated by the radiograph 76. In the preferred embodiment, the second template 62 may be a series of templates containing the images in the different sizes of the metaphyseal segments 14 so the surgeon can select which size metaphyseal segment 14 most closely fills the metaphysis 60 of the host femur 78.

Once the second template 62 is oriented on the radiograph 76 in the manner described above, the position of the superior surface of the greater trochanter 82 of the host femur 78, as indicated by the radiograph 76, may be compared to the longitudinal scale 68 on the second template 62. By recording the location of the superior surface of the greater trochanter 82 as appearing on the longitudinal scale 68, the surgeon can determine the depth to which the intramedullary canal must be reamed to accommodate the modular hip prosthesis 10 in the manner described below. In addition, the diagonal scale 72 on the second template 62 may be used to indicate the particular size of the modular head 16 that should be used to most closely mate with the geometry of the pelvis. As will be appreciated by those skilled in the art, if the surgeon determines that there is to be no change in the length of the neck region of the femur, the point marking the center of the femoral head, which is the closest to the center of the acetabulum, indicates the appropriate neck length to choose. If lengthening is required, the neck length that places the center of the head 82 of the host femur 78 on the second template 62 above the center of the acetabulum template is preferred. Should it be necessary to shorten the length, a femoral neck length is selected that places the center of the head 84 of the host femur 78 below the center of the acetabulum of the template is preferred.

Figures 7B, 7C, 7D:
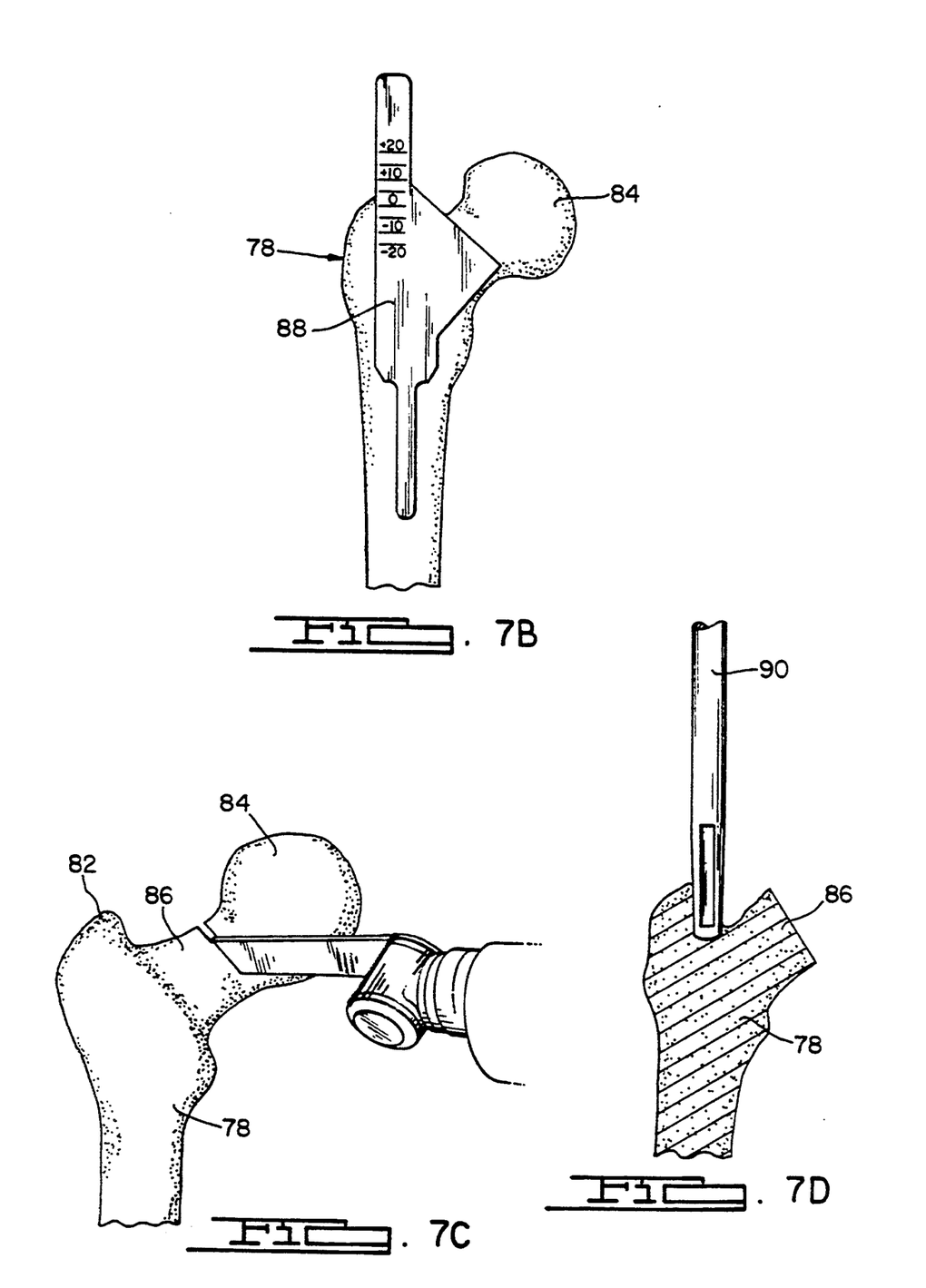

Once the first and second templates 56 and 62 have been used in the manner described above, a Steinmann pin (not shown) is placed over the iliac wing above the acetabulum. The Steinmann pin is bent so that it can be used to mark a position on the greater trochanter 82 which is then turned out of the operative field. After the hip is dislocated, the head 84 of the host femur 78 is resected such that most or all of the neck portion 86 of the host femur 78 is retained as shown in FIG. 7(C). By retaining as much of the neck portion 86 of the host femur 78 as possible, the moment arm of the host femur 78, which is able to resist torsional loading, is longer than it would be if the neck portion 86 were removed. A resection overlay 88 can be used to estimate the angle and the position of the osteotomy by lining the preoperatively-determined position with the tip of the greater trochanter as shown in FIG. 7(B).

After the host femur 78 has been resected in the manner described above, a hollow punch 90 is located on the superior surface of the host femur 78 as shown in FIG. 7(D). A force is then applied to upper surface hollow punch 90 in order to form an indentation in the superior surface of the host femur 78. The indentation formed by the hollow punch 90 is used to establish a point of entry for the different reamers used for forming the diaphyseal cavity 92 in the intramedullary canal as described below. The indentation should be lateralized so that varus positioning of the femoral component is avoided.

Once the indentation has been made on the superior surface of the host femur 78, the acetabular component (not shown) is implanted in a manner known in the art. In this regard, a partial superior and anterior capsulotomy is performed to allow exposure of the anterior acetabular rim in a conventional manner. The acetabulum is then reamed with the largest reamer (not shown) that easily fits within the acetabulum and is continued until concentric removal of all the remaining acetabular cartilage and the exposure of the punctate bleeding of the subchondral plate is achieved. A metal frame shell gauge (not shown) corresponding to the last reamer used is then inserted into the acetabulum. The appropriate component position is then judged using a downsized acetabular gauge, which can be easily inserted and positioned in the acetabulum allowing removal of any overhanging anterior, posterior or superior osteophytes. The acetabular shell is locked onto the acetabular positioner (not shown) and driven into the fully seated positioned. When located in this manner, it should not be possible to twist the acetabular shell within the bone with the acetabular positioner. If screws are then used to supplement fixation, they should be placed in the superior-posterior region so as to avoid inadvertent protrusion of the screws. The screws should not be placed in the anterior hole of the acetabulum.

Figures 7E, 7F, 7G, 7H, 7I, 7J:
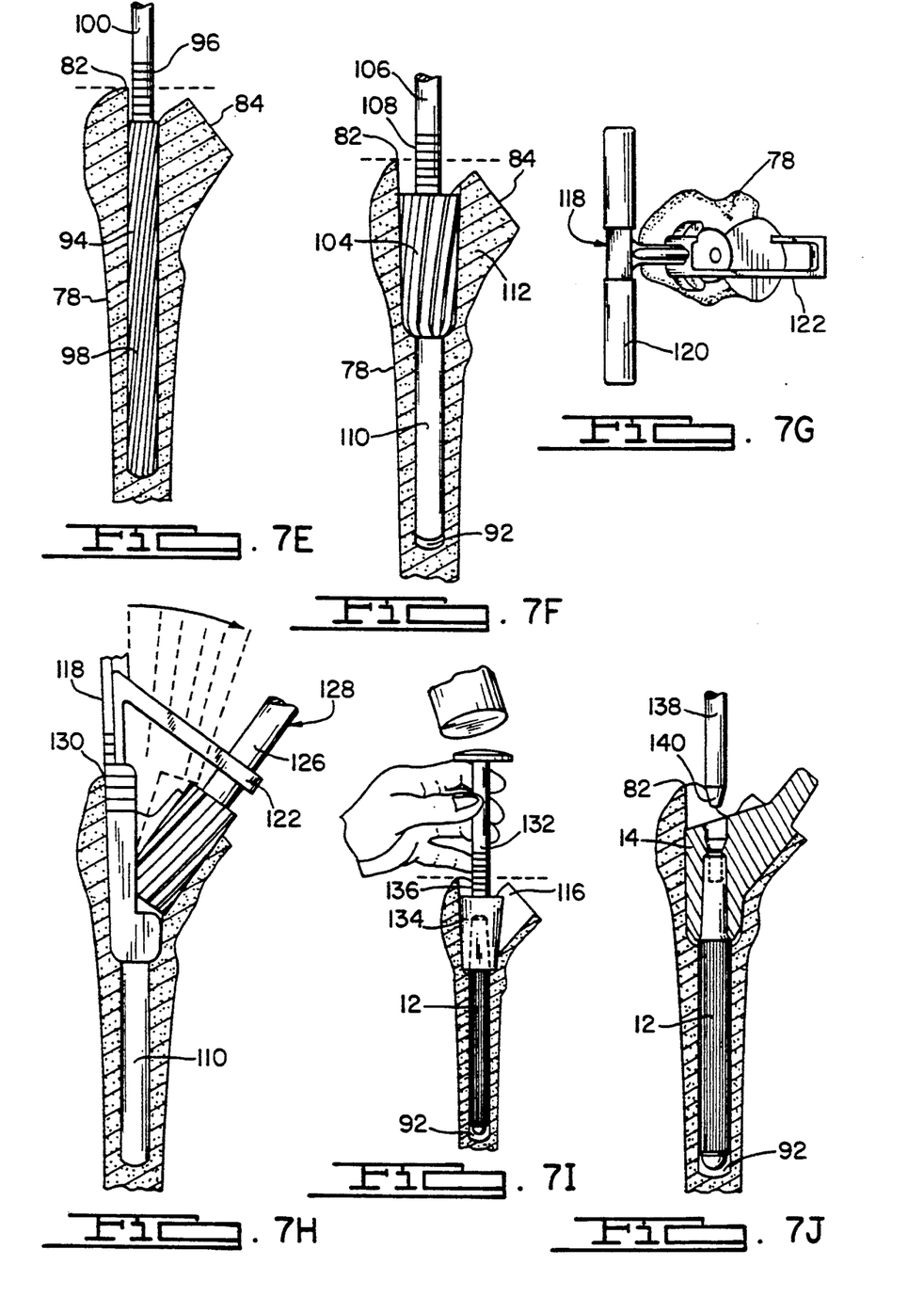

Once the acetabular component is secured, a distal canal reamer 94 having scaled markings 96 is positioned in the indentation formed by the hollow punch 90. As shown in FIG. 7(E), the distal canal reamer 94 includes a plurality of spiral cutting flutes 98 and a shaft portion 100. The spiral cutting flutes 98 are operable to pass debris out of the diaphyseal cavity 92 during reaming. The scaled markings 96 on the distal canal reamer 94 correspond to the particular size of the metaphyseal segment 14 that is being used. The scaled markings 96 permit the surgeon to easily identify when the diaphyseal cavity 92 has been reamed to the appropriate depth by comparing the appropriate marking on the shaft portion with the upper surface of the greater trochanter 82. As one skilled in the art will appreciate, the surgeon may elect to ream the intramedullary canal slightly deeper if the surgeon so chooses. The distal canal reamer 94 is preferably one of a plurality of reamers which are of different sizes and which are used in a sequential manner until the hard cortical bone is contacted of the distal end of the diaphyseal cavity 92.

Once the diaphyseal cavity 92 has been prepared for receiving the diaphyseal segment 12, an additional portion of the host femur 78 must be removed for accepting axial cone portion 28 of the metaphyseal segment 14. To remove this additional portion of the host femur 78, a metaphyseal reamer 102 is used as shown in FIG. 7(F). The metaphyseal reamer 102 is shown having a fluted section 104 and a superior shaft section 106 that is disposed superiorly with respect to the fluted section 104. The inferior portion of the shaft section 106 includes scaled markings 108 that correspond to the scaled markings 70 on the second template 62. The metaphyseal reamer 102 further includes a removable alignment shaft 110 which is able to be inserted into the diaphyseal cavity 92 so as to align the metaphyseal reamer 102 with respect to the diaphyseal cavity 92. Once the metaphyseal reamer 102 is positioned at the superior portion of the diaphyseal cavity 92, the metaphysis 112 is reamed with the metaphyseal reamer 102 so as to form metaphyseal cavity 116. The surgeon can determine the proper depth of reaming by comparing the scaled markings 108 on the superior shaft portion 106 (which corresponds to the scaled markings 70 on the longitudinal scale 68 of the second template 62) to the superior surface of the greater trochanter 82. Once the metaphyseal cavity 116 has been formed, the metaphyseal cavity 116 is inspected to ensure that the cortical bone has been exposed on the anterior inner surface of the host femur 78.

After the metaphysis 112 has been reamed, it is necessary to ream the neck portion 86 of the host femur 78 so as to accommodate the cervical cone portion 30 of the metaphyseal segment 14. For this operation, a femoral neck cutting guide 118 is used as shown in FIG. 7(G) and (H). The femoral neck cutting guide 118 includes a handle section 120 and a C-shaped alignment arm 122 which extends medially from the handle section 120. In addition, the femoral neck cutting guide 118 which is able to engage the removable alignment shaft 110 of the metaphyseal reamer 102 so as to align the femoral neck cutting guide 118 with respect to the diaphyseal cavity 92. As shown in FIG. 7(G), the alignment arm 122 includes an entry for a femoral neck reamer 126. The femoral neck reamer 126 has an outer sleeve 128 which remains rotationally stationary while the femoral neck reamer 126 is being used. The outer sleeve 128 of the femoral neck reamer 126 cooperates with the alignment arm 122 so as to ream the neck portion 86 of the host femur 78 in a constant profile in the anterior-posterior view, yet permitting the cross-section to vary in the medial-lateral view. The outer sleeve 128 of the femoral neck reamer 126 is used to prevent metal-to-metal contact between the femoral neck reamer 126 and the alignment arm 122. In addition, the outer sleeve 128 may be of different thicknesses so as to limit the travel of the femoral neck reamer 126 within the alignment arm 122 so as to remove a predetermined portion of the metaphysis 112. This ensures that the size of the metaphyseal cavity 116 corresponds to the size of the metaphyseal segment 14 that is to be used. For this reason, the thickness of the outer sleeve 128 may vary with the size of the metaphyseal segment 14 and may be color coded to indicate the particular size of the femoral neck reamer 126. While the outer sleeve 128 may be made from acetyl copolymer, other suitable materials may be used.

Once the femoral neck cutting guide 118 is inserted into the diaphyseal cavity 92 and is aligned with the neck portion 86 of the host femur 78 by gently tapping the femoral neck cutting guide 118 with a mallet, the femoral neck reamer 126 is positioned within the alignment arm 122 of the femoral neck cutting guide 118. The femoral neck reamer 126 is then slowly displaced laterally to ream the cancellous bone of the neck portion 86 of the host femur 76. Generally, it is necessary to use more than one femoral neck reamer 126 (e.g., a smaller reamer with a cylindrical head and then a larger reamer with a tapered head) in order to ensure that the cortical bone is properly exposed, with the smaller size reamer being used first. The femoral neck cutting guide 118 also has scaled markings 130 which allows the surgeon to determine proper depth at which reaming of the neck portion 86 is to begin.

The use of the femoral neck cutting guide 118 improves the uniformity to which the metaphyseal cavity 116 may be formed. This is because the femoral neck cutting guide 118 allows the axis of the portion of the metaphyseal cavity 116 which is to receive the axial cone portion 28 of the metaphyseal segment 14 to intersect at a predetermined position the axis of the portion of the metaphyseal cavity 116 which is to receive the cervical cone portion 30. Accordingly, the resulting metaphyseal cavity 116 is able to more closely mate with the geometry of the metaphyseal segment 14.

Once the diaphyseal cavity 92 and the metaphyseal cavity 116 are prepared in the manner described above, the surgeon is able to confirm the appropriate selection of the size of the diaphyseal segment 12 and the metaphyseal segment 14 by trial placements using the alignment shaft 110 of the metaphyseal reamer 102. The diaphyseal segment 12 then is inserted into host femur 78 such that the slotted section 24 is positioned in a medial-lateral alignment. The diaphyseal segment 12 is gently tapped down to a location approximately 5 mm above its final insertion depth by using a distal stem driver 134 that is sized according to the particular metaphyseal segment being used. The distal stem driver 132 includes a lower head portion 134 with an insert (not shown) that fits around the tapered portion 20 of diaphyseal segment 12 so as to provide uniform pressure to the diaphyseal segment 12 when a force is applied to the upper surface of the distal stem driver 132. While the insert may be made from acetyl homopolymer, other suitable materials may be used. In addition, the distal stem driver 132 includes scaled markings 136 that correspond to the scaled markings 70 on the second template 62. The scaled marking 136 are used by the surgeon to ensure that the diaphyseal segment 12 is located approximately 5 mm of its final insert depth.

Figure 7K:
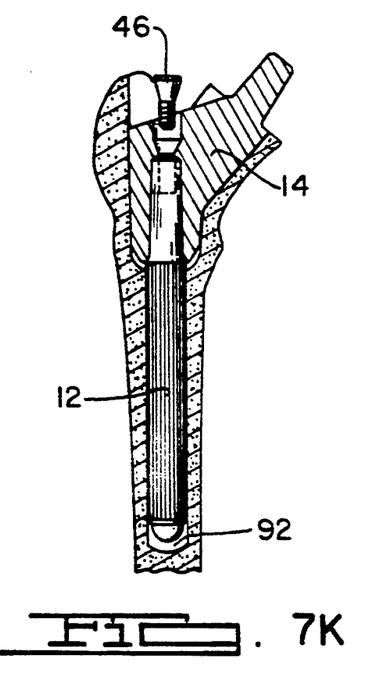

The metaphyseal segment 14 is then impacted into host femur 78 by the use of a metaphyseal inserter 138 as shown in FIG. 7(J). Impacting the metaphyseal segment 14 using the metaphyseal inserter 138 locks the diaphyseal segment 12 to the metaphyseal segment 16. The metaphyseal inserter 138 may have an end portion 140 which may be removed so that a corresponding threaded end portion (not shown) may be disposed on the metaphyseal inserter 138. This permits the metaphyseal inserter 138 to also be used to remove the metaphyseal segment 14 by causing the threaded end portion to engage the threaded bore 50 of the diaphyseal segment 12 and then axially displacing the metaphyseal inserter 138 such that the diaphyseal segment 12 and the metaphyseal segment 14 are removed. Final seating of the metaphyseal segment 16 includes the insertion of the segmental locking screw 46 as shown in FIG. 7(K) which is followed by the placement of the modular head 16 onto the neck portion 32 of the metaphyseal segment 14. The modular hip prosthesis 10 is now in position to be engaged with the hip socket of the patient.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A set of surgical instruments for use in implanting a hip prosthesis in a host femur having a neck portion, said hip prosthesis including a diaphyseal segment and a metaphyseal segment, said set of surgical instruments comprising:

a distal canal reamer operable to ream a cavity in said host femur for receiving said diaphyseal segment of said hip prosthesis;

a metaphyseal reamer operable to ream a cavity in said host femur for receiving a portion of said metaphyseal segment;

a femoral neck reamer operable during lateral displacement thereof to ream said neck portion of said host femur for receiving a portion of said metaphyseal segment said femoral neck reamer having an outer sleeve; and a femoral neck cutting guide operable to be used in conjunction with said femoral neck reamer to ream said neck portion, said femoral neck cutting guide including a medially extending alignment arm being operable to guide lateral displacement of said femoral neck reamer.

2. The set of surgical instruments according to claim 1 wherein the size of said outer sleeve is proportional to the size of said metaphyseal segment.

3. The set of surgical instruments according to claim 1, wherein said outer sleeve of said femoral neck reamer is operable to engage said femoral neck cutting guide so as to cause said femoral neck femur to form a cavity in said host femur having a substantially uniform cross-section in the anterior-posterior view while having a varying cross-section in the medial-lateral view.

4. The set of surgical instruments according to claim 1, further including template having a plurality of scaled markings disposed thereon which are operable to establish the proper location of said hip prosthesis within said host femur, said femoral neck cutting guide further comprises a plurality of scaled markings which positionally correspond to said scaled markings on said template.

5. The set of surgical instruments according to claim 1, further including a distal stem driver for inserting said diaphyseal segment into said host femur.

* * * * *